Figure 1:
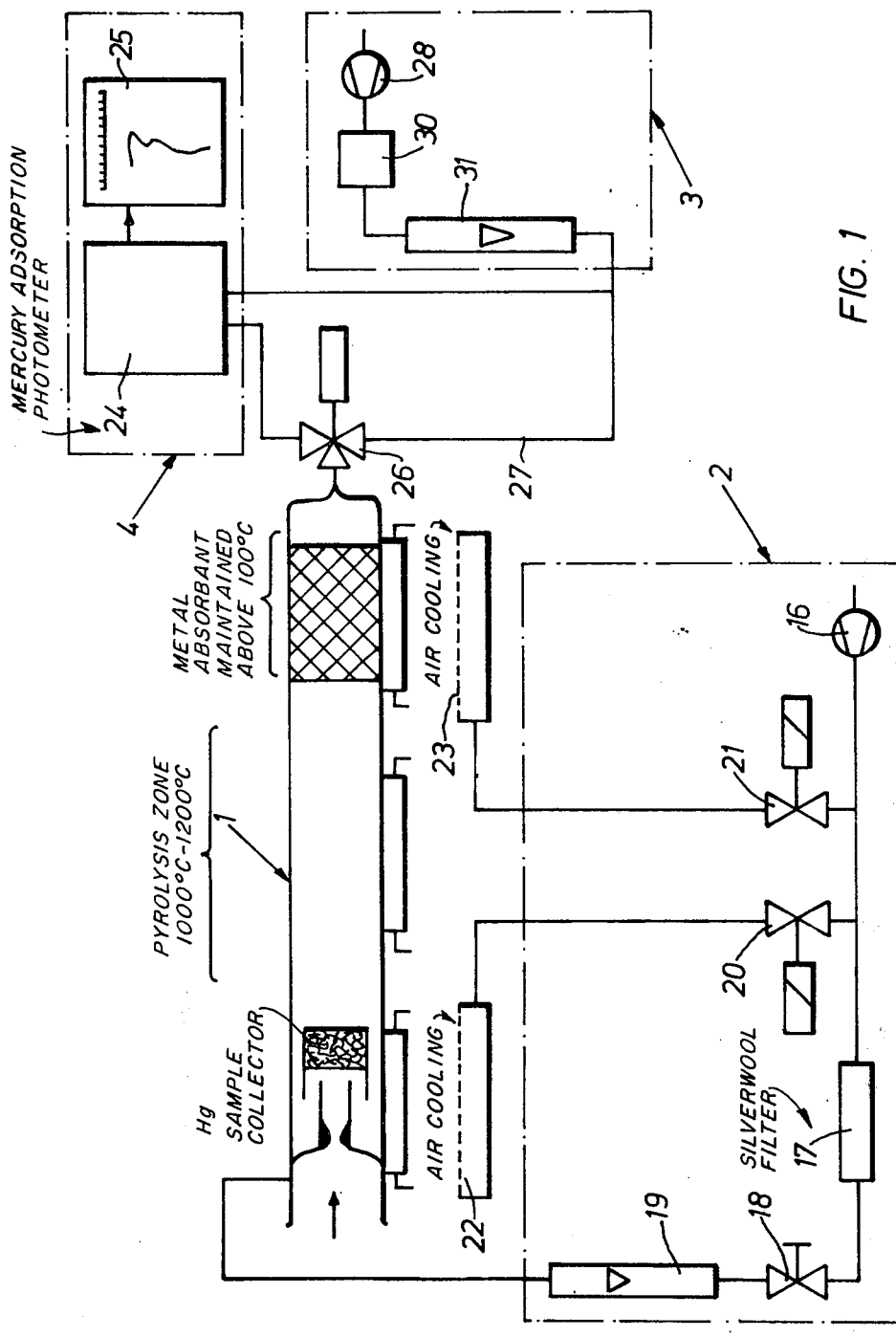

United States Patent [19]
Becker et al.

[11] 4,023,929
[45] May 17, 1977

[54] PROCESS FOR DETERMINING TRACES OF MERCURY IN LIQUIDS

[75] Inventors: Wolf-Jürgen Becker; Kurt Schreckling, both of Leverkusen, Germany

[73] Assignee: Bayer Aktiengesellschaft, Leverkusen, Germany

[22] Filed: Aug. 27, 1975

[21] Appl. No.: 608,311

[30] Foreign Application Priority Data

Sept. 4, 1974 Germany .......................... 2442346

[52] U.S. Cl. ..................... 23/230 PC; 23/232 R; 23/253 PC; 23/254 R
[51] Int. Cl.² ............... G01N 31/12; G01N 31/06; G01N 33/18
[58] Field of Search ..... 23/230 PC, 253 PC, 232 R, 23/254 R

[56] References Cited
UNITED STATES PATENTS

| | | | |
|---|---|---|---|
| 3,565,583 | 2/1971 | McNulty et al. | 23/230 PC |
| 3,884,639 | 5/1975 | Sugiyama | 23/254 R X |
| 3,933,431 | 1/1976 | Trujillo et al. | 23/232 R |
| 3,957,441 | 5/1976 | Baba | 23/230 PC X |

OTHER PUBLICATIONS

Lidums et al., "Mercury Analysis in Biological Material by Direct Combustion in Oxygen and Photometric Determination of the Mercury Vapour," Acta Chem. Scand. 22(1968), No. 7, pp. 2150–2156.
Thomas et al., "Rapid Pyrolytic Method to Determine Total Mercury in Fish," Anal. Chem., vol. 44, No. 3, Mar. 1972, pp. 512–514.

*Primary Examiner*—Norman Yudkoff
*Assistant Examiner*—Barry I. Hollander
*Attorney, Agent, or Firm*—Burgess, Dinklage & Sprung

[57] ABSTRACT

In a process for determining the total mercury content in samples of effluent water, the sample is collected on a sample collector where it is evaporated at 1000° C before it is decomposed in a pyrolysis zone at 1000° to 1200° C. The mercury in the liquid sample is thereby expelled as vapor and together with carrier gas it is conducted over a metal sheet which absorbs the mercury and concentrates it. The concentrated mercury is then expelled by heating the metal and transferred by the carrier gas into a mercury absorption photometer where it is determined quantitatively.

12 Claims, 2 Drawing Figures

PROCESS FOR DETERMINING TRACES OF MERCURY IN LIQUIDS

This invention relates to a process and apparatus for determining the total mercury content in liquids and in particular for determining traces of mercury in water and effluent.

The controlled treatment and purification of effluent is possible only if the concentrations of impurities can be determined quantitatively and as far as possible continuously. This requires the accurate determinations of numerous components. Many of these impurities must be detected at high dilutions (one millionth to one thousand millionth) with very sensitive analytical instruments, The determination of traces of mercury in liquids and especially water is particularly important on account of its high toxicity.

Organically and inorganically bound mercury in liquids can be chemically decomposed into gaseous mercury and determined at a wavelength of 253.7 nm by non-flame atomic absorption. This method can be used for detecting concentrations as low as one part in a thousand million. See D. C. Manning "Non-flame methods for mercury determination by atomic absorption — a review" Atomic Absorption 9 (1970) 5, 97/99). Inorganically bound mercury is preferably reduced to atomic mercury with tin(II)chloride solutions. The decomposition of organic mercury compounds requires a considerable outlay of chemical reagents. The analytical determinations are very time-consuming and even then the conversion into free mercury is in most cases incomplete. After the chemical reaction, the atomic mercury is blown out with a carrier gas. Several mercury analysers operating with chemical decomposition are already known. These automatic analytical instruments for the continuous monitoring of effluent or process streams are very expensive and will therefore be restricted in their application.

From work carried out by the present Applicants and only recently published it is known that pyrolytic mercury analysis is much simpler than the previous wet chemical methods. See German Offenlegungsschrift No. 2,261,456.

The sample which contains mercury is decomposed in a combustion furnace at about 1000° C to 1200° C and the resulting mercury vapour is transferred to a mercury absorption photometer. This method of direct analysis can be used for measuring concentrations down to 2 milligrams of mercury per liter but is not suitable for the much lower concentrations occurring in river water or drinking water, in which even concentrations of a few nanograms per liter must be detectable, which corresponds to a threshold of measurement of 0.1 milligram per liter or less. At this range of concentrations, difficulties arise when the previous process is employed.

When the traces of mercury are present at such low concentrations, non-specific absorptions of accompanying substances (e.g. water vapour or dust) interfere with the non-flame atomic absorption at the wavelength 253.7 nm.

Due to incomplete pyrolysis, which is inherent in the system, only a certain but reproducible proportion of the mercury is transferred to the measuring cup of the analytical instrument. At the same time, washing out effects may occur.

It is also known that mercury vapour can be made to accumulate on metal, whereby much smaller mercury concentrations can be detected. Methods employing copper, silver or gold adsorbers are already known. See H. Brandenburger, H. Bader "Determination of nanogramme quantities of mercury from solutions by a flameless atomic absorption process" Helv. Chim.Acta 50 (1967) 5, 1409/1415; O. I. Ioensuu "Mercury-Vapor Detector" Appl. Spectr. 15 (1971) 5, 526/528).

In the method described in H. Brandenburger, H. Bader "Determination of nanogramme quantities of mercury from solutions by a flameless atomic absorption process" the mercury in solution is amalgamated on a copper coil dipped into the solution. The coil is subsequently heated and the mercury thereby liberated as vapour is determined spectro-photometrically. This method, however, is suitable only for few liquids because reproducible results can be obtained by this method only if the metal mesh or wire has a constant capacity for amalgamation, and it is obvious that amalgamation can be completely prevented, for example by corrosion in corrosive liquids including certain effluents. The method described in H. Brandenburger, H. Bader "Determination of nanogramme quantities of mercury from solutions by a flameless atomic absorption process" is therefore not applicable to the present case. In the method described in the literature reference O. I. Ioensuu "Mercury-Vapor Detector" the solid sample is burnt at low temperature together with a piece of paper which has been soaked in alcohol, and the mercury thereby liberated is again determined quantitatively in a mercury adsorption photometer after it has been concentrated on a gold sheet. This method of combustion cannot be used for liquid samples. A wet chemical method of decomposition is therefore proposed in O. I. Ioensuu, "Mercury-Vapor Detector" for the analysis of liquid samples.

The problem which the invention sets out to solve is to determine the total mercury content of liquids at concentrations of a few nanogramme per liter and to develop an apparatus for the routine carrying out of such analyses.

According to the invention, there is provided a process for the determination of the total mercury content of liquids, wherein the liquid sample to be analysed is collected in a sample collector, subsequently evaporated by heating to temperatures above 1000° C and transferred by a carrier gas into a pyrolysis zone at a temperature of from 1000° to 1200° C, where the sample is decomposed and the mercury contained in the sample is expelled as vapour, and the carrier gas together with the resulting mercury vapour is passed over a metal on which the mercury is absorbed and from which the mercury is subsequently desorbed by heating to be transferred by the carrier gas into a mercury absorption photometer where it is determined quantitatively.

The carrier gas used is preferably atmospheric air which has been passed through silver wool to remove any traces of mercury before it is mixed with the sample to be analysed. It has been found that the metal, which may be in the form of mesh or sheet, used for absorbing and concentrating the mercury should preferably be kept at a temperature above 100° and more preferably at 150° C. This elevated temperature prevents the condensation of water vapour which would prevent amalgamation.

According to a preferred embodiment of the invention the combustion products of the liquid sample are made to bypass the mercury adsorption photometer during the process of pyrolysis so that only vapour desorbed from the metal wire or sheet is introduced into the mercury adsorption photometer.

According to the invention, there is also provided an apparatus for the determination of the total mercury content of liquids, comprising a heated reaction chamber, comprising an input zone containing a sample collector in which a liquid sample is collectd and subsequently evaporated, a pyrolysis zone and a mercury sorption containing a metal, a mercury adsorption photometer connected to the reaction chamber and means for passing a carrier gas through the reaction chamber and the photometer.

The input zone is preferably open to the atmosphere and is provided in its interior with an inlet aperture which opens into a supporting tube for the introduction of an injection needle used for introducing the sample. The sample collector is arranged at the end of this tube.

The arrangement described above enables a fully automatic analysis to be carried out within a few minutes. An optimum analysis cycle may cover a period of, for example, 6 minutes. This limit of detection is approximately 2 micrograms per liter when 20 microliter of sample are introduced. In accordance with the VDI guidelines, the limit of detection was taken as three times the standard deviation of the zero point fluctuations between two analyses.

The special device provided for injecting the sample without any rubber caps or similar seals which have to be perforated ensures that no residue of sample containing mercury can be left in the input zone after an analysis to falsify a subsequent analysis. Moreover, an efficiency of more than 90% is achieved with this input device.

When the arrangement is used in conjunction with commercial mercury-ultraviolet atomic absorption photometers, the range of measurement can be adjusted to 0.1 milligram of mercury per liter on a 20 microliter sample. This corresponds to 2 nanograms of mercury per sample. In this range of measurement, the standard deviation is better than 4%, the standard deviation of injection with a commercial microliter injection needle being between 0.5 and 1%.

Figure 2:
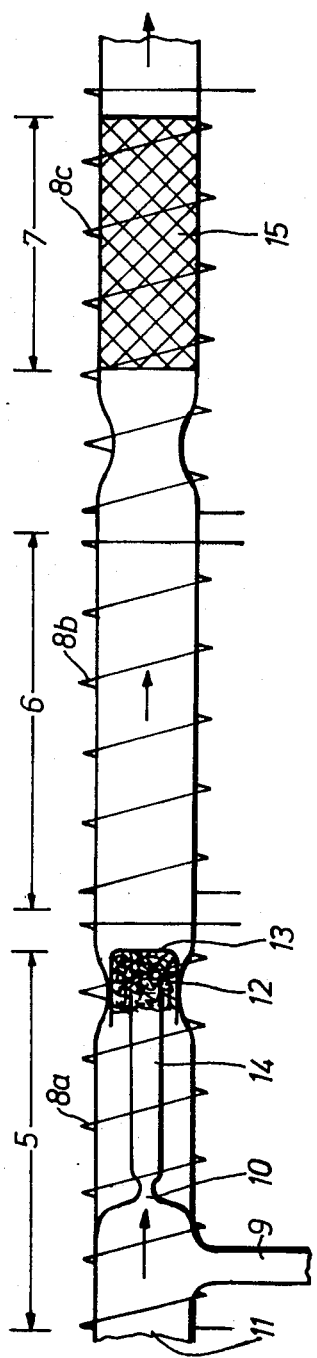

An example of the invention will now be described in more detail with reference to the drawings, in which:

FIG. 1 is a block circuit diagram of an apparatus used for determining traces of mercury in effluent and FIG. 2 shows a reaction chamber for the combustion and concentration of mercury.

The apparatus for mercury determination shown in FIG. 1 consists basically of a reaction chamber 1, an apparatus 2 for producing a stream of carrier gas, an apparatus 3 for absorbing the stream of carrier gas by suction and a measuring and recording device 4. The main part of the apparatus is the quartz reaction chamber 1 comprising an input zone 5, a pyrolysis zone 6 and a sorption zone 7 (see FIG. 2). Each of these three zones is surrounded by a concentric heating coil 8 of platinum wire. To ensure rapid heat exchange, the reaction chamber 1 is made of thin-walled quartz glass, preferably with a wall thickness of 1 mm and an internal diameter of about 12 mm. Dry air free from mercury is continuously sucked through the reaction chamber 1 as carrier gas. For this purpose, the input zone 5 is charged with purified atmospheric air at a slight excess pressure.

To prevent air from the surrounding room being sucked into the reaction chamber 1, an excess of carrier gas is fed into the input zone 5 through the inlet 9, preferably at 200 liters per hour. A pump 28 produces a constant vacuum in the reaction chamber 1 (see FIG. 1). This vacuum causes a partial stream of the carrier gas to be sucked into the reaction chamber 1 through the inlet 10, preferably at the rate of 30 liters per hour. The remaining carrier gas escapes to the outside through the aperture 11 of the input zone 5. A microliter syringe is used to inject a sample of effluent through the inlet aperture 10 into a mass of quartz wool 12 in a sample collector 13. Instead of quartz wool, the sample collector 13 may equally well be fitted with quartz chips or ceramic granules. In order to obtain constant conditions of injection, a support tube 14 is provided behind the inlet aperture 10 for the introduction of the needle of the syringe. The diameter of the inlet aperture 10 is constricted so that the flow velocity of the carrier gas is increased sufficiently to prevent any aerosol escaping when the sample is injected. The diameter of the constriction is preferably 1 mm.

The heating coil 8b of the pyrolysis zone 6 is switched on before the effluent water is injected. The temperature in this zone is between 1000° and 1200° C. The following sorption zone 7 contains a gold wire mesh 15 for concentrating the mercury. The heating-up of the carrier gas in the preceding pyrolysis zone 6 causes the sorption zone with gold wire mesh 15 to assume a temperature of about 150° C.

After a sample has been injected, the heating coil 8a of the input zone 5 is switched on. The heating power is adjusted so that the maximum temperature of 1000° C is reached after only 1 minute. The sample is thereby continuously evaporated and inorganically or organically bound mercury is partly liberated in atomic form and reaches the required temperature for complete decomposition in the previously heated pyrolysis zone. The relatively slow rise in temperature of the input zone 5 ensures that the reaction products will remain for a sufficiently long time in the pyrolysis zone 6 and prevents escape through the inlet aperture 10. Furthermore, the high final temperature of the input zone 5 ensures that all the constituents of the sample enter the pyrolysis zone 6 and sorption zone 7. In zone 7, the atomic mercury is amalgamated on the concentrically arranged gold wire mesh 15. Amalgamation is carried out at a temperature of 150° C in order to prevent condensation of water vapour in this zone. Condensation of water vapour would interfere with the amalgamation of the gold wire mesh. The carrier gas is subsequently discharged together with the products of combustion and discarded.

Desorption of the mercury which has accumulated on the gold wire mesh may be carried out after the mercury vapour has washed over the wire for a sufficient length of time. To desorb the mercury, the gold wire mesh 15 is heated by the heating coil 8c. The mercury is thereby liberated in the atomic form and can be transferred by the carrier gas to a suitable mercury gas analysis apparatus. Since the initial temperature is 150° C, the desorption temperature is reached within a few seconds so that a high localised mercury concentration peak is produced. During the desorption phase, all three zones 5, 6 and 7 are heated to about 1000° C to prevent the deposition of residues.

The auxiliary devices 2 and 3 for producing and sucking off the stream of carrier gas will now be described in more detail (see FIG. 1). The gas pump delivers purified atmospheric air into the input zone 5 of the reaction chamber 1 through a silver wool filter 17, an adjustment valve 18 and a flowmeter 19. The silver wool filter 17 ensures that the stream of carrier gas will be free from mercury. The rate of gas flow is preferably 200 liters per hour. The carrier gas introduced by a pump 16 is branched off at valves 20 and 21 to form two streams which may be carried to air nozzles 22 and 23. These air streams are used for rapidly cooling the heating means in the input zone 5 and sorption zone 7 so that the analytical cycle can be speeded up.

Determination of the mercury collected in the sorption zone is carried out in the measuring and recording device 4. This consists of a mercury analysis instrument 24 and a recording instrument 25. The mercury analysis instrument used may suitably be an adsorption photometer and which detects atomic mercury at a wavelength of 253.7 nm by means of nonflame atomic absorption.

An electromagnetically operated three-way valve 26 is provided at the output end of the reaction chamber 1. It communicates with the suction pump 28 either through the throughflow cup of the mercury adsorption photometer 24 or through a bypass 27. In addition, a flow regulator 30 and a flowmeter 31 are connected into the path from valve 26 to pump 28. The gas pump 28, flow regulator 30 and flowmeter 31 cooperate to cause a constant stream of carrier gas to be sucked through the reaction chamber 1, preferably at the rate of 30 liters per hour.

The three-way valve 26 is controlled so that the outlet of the reaction chamber is connected to the mercury adsorption photometer 24 only during the desorption phase. During the sorption phase, the carrier gas is passed through the bypass 27 to prevent contamination of the sensitive mercury adsorption photometer 24.

After manual injection of the sample, the analytical cycle is automatically controlled by starting an electric programme control. The programme has a duration of about 6 minutes and runs as follows:

1. Injection of sample
2. Start of electric programme control by pressing button
3. Heating up input zone 5, duration 120 seconds
4. Cooling of input zone 5, duration to end of cycle; and switching carrier gas to mercury adsorption photometer duration 70 seconds
5. 20 seconds after switching over the stream of carrier gas, switching on heating of sorption zone 7, duration 40 seconds
6. after switching carrier gas to bypass 27; switching on cooling air for sorption zone 7, duration 120 second
7. switching off cooling air for input zone 5 and sorption zone 7
8. apparatus ready for fresh cycle.

The apparatus according to the invention for determining mercury traces has the following advantages in addition to those described above:

1. The special design of the input zone 5 without rubber membranes or caps to be perforated ensures that no traces of sample contaminated with mercury will be left in the input zone 5 after an analytical cycle to falsify the analytical results of the following cycle. Furthermore, the degree of efficiency achieved with this technique of introducing the sample is greater than 90%. The special method of conducting the carrier gas in the input zone 5 prevents the entry of contaminated atmospheric air into reaction chamber 1.

2. The use of simple platinum heating wires in direct contact with the quartz reaction chamber 1 ensures rapid temperature adjustment in the individual heating zones. Cooling between analytical cycles can be substantially, accelerated by cooling air (from nozzles 22 and 23). The apparatus is therefore rapidly ready for use again and analyses can be carried out in rapid sequence.

3. The construction of the apparatus fulfils all the conditions necessary for fully automatic analysis which can be achieved simply by equipping the input zone 5 with a commercial dosing or injection valve.

What we claim is:

1. A process for the determination of the total mercury content of liquids, wherein the liquid sample to be analysed is collected in a sample collector, subsequently evaporated by heating to temperatures above 1000° C and transferred by a carrier gas into a pyrolysis zone which is maintained at a pyrolysis temperature of from 1000° to 1200° C, and in which the sample is decomposed and the mercury contained in the sample is liberated as mercury vapour, and the carrier gas together with the mercury vapour is passed over a metal maintained at a temperature above 100° C. on which the mercury is absorbed and from which the mercury is subsequently desorbed by heating and transferred by the carrier gas into a mercury adsorption photometer where the mercury is determined quantitatively.

2. A process as claimed in claim 1, wherein the carrier gas is atmospheric air which has been passed through silver wool to remove any traces of mercury from it.

3. A process as claimed in claim 1, wherein said metal is kept at a temperature of substantially 150° C.

4. A process as claimed in claim 1, wherein during the pyrolysis, the products of combustion of the liquid sample bypass the mercury adsorption photometer so that only the mercury vapour desorbed from the metal is introduced into the mercury adsorption photometer.

5. Process of claim 1, wherein the carrier gas containing the liberated mercury vapour, which is formed in the pyrolysis zone is introduced directly from the pyrolysis zone into the metal for absorption of the mercury.

6. Process of claim 2, wherein the carrier gas containing the liberated mercury vapour, which is formed in the pyrolysis zone is introduced directly from the pyrolysis zone into the metal for absorption of the mercury.

7. Process of claim 3, wherein the carrier gas containing the liberated mercury vapour, which is formed in the pyrolysis zone is introduced directly from the pyrolysis zone into the metal for absorption of the mercury.

8. Process of claim 4, wherein the carrier gas containing the liberated mercury vapour, which is formed in the pyrolysis zone is introduced directly from the pyrolysis zone into the metal for absorption of the mercury.

9. Process of claim 5, wherein the gas is heated in the pyrolysis zone, and the heating in the pyrolysis zone causes the metal on which the mercury is absorbed to assume said temperature of above 100° C.

10. Process of claim 6, wherein the gas is heated in the pyrolysis zone, and the heating in the pyrolysis zone causes the metal on which the mercury is absorbed to assume said temperature of above 100° C.

11. Process of claim 7, wherein the gas is heated in the pyrolysis zone, and the heating in the pyrolysis zone causes the metal on which the mercury is absorbed to assume said temperature of above 100° C.

12. Process of claim 8, wherein the gas is heated in the pyrolysis zone, and the heating in the pyrolysis zone causes the metal on which the mercury is absorbed to assume said temperature of above 100° C.

* * * * *

UNITED STATES PATENT AND TRADEMARK OFFICE
CERTIFICATE OF CORRECTION

PATENT NO. : 4,023,929

DATED : May 17, 1977

INVENTOR(S) : Wolf-Jürgen Becker and Kurt Schreckling

It is certified that error appears in the above-identified patent and that said Letters Patent are hereby corrected as shown below:

Column 5, line 3, after "pump" insert --16--.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*